(12) United States Patent
Bernard

(10) Patent No.: US 11,052,209 B2
(45) Date of Patent: Jul. 6, 2021

(54) FACIAL INTERFACE

(71) Applicant: 9310-3760 QUEBEC INC., Brossard (CA)

(72) Inventor: Louise Bernard, Boucherville (CA)

(73) Assignee: 9310-3760 QUEBEC INC., Brossard (CA)

( * ) Notice: Subject to any disclaimer, the term of this patent is extended or adjusted under 35 U.S.C. 154(b) by 251 days.

(21) Appl. No.: 16/068,229

(22) PCT Filed: Jan. 5, 2017

(86) PCT No.: PCT/CA2017/050007
§ 371 (c)(1),
(2) Date: Jul. 5, 2018

(87) PCT Pub. No.: WO2017/117673
PCT Pub. Date: Jul. 13, 2017

(65) Prior Publication Data
US 2019/0009045 A1    Jan. 10, 2019

Related U.S. Application Data

(60) Provisional application No. 62/275,526, filed on Jan. 6, 2016.

(51) Int. Cl.
*A61M 16/06* (2006.01)
*A61F 5/08* (2006.01)

(52) U.S. Cl.
CPC .......... *A61M 16/0605* (2014.02); *A61F 5/08* (2013.01); *A61M 16/06* (2013.01); *A61M 16/0616* (2014.02); *A61M 16/0633* (2014.02); *A61M 2205/02* (2013.01); *A61M 2205/0238* (2013.01)

(58) Field of Classification Search
CPC combination set(s) only.
See application file for complete search history.

(56) References Cited

U.S. PATENT DOCUMENTS 3,768,100 A * 10/1973 Colman ............. A41D 13/1161
                                                                    2/9
6,082,360 A *  7/2000 Rudolph ............... A61M 16/06
                                                                 128/206.24

(Continued)

FOREIGN PATENT DOCUMENTS

AU      2009202232     12/2009
CA      2819723 A1     11/2014

(Continued)

OTHER PUBLICATIONS

International Search Report of PCT/CA2017/050007; Gatineau; dated Feb. 1, 2017; Cote, Alexis.

(Continued)

*Primary Examiner* — Margaret M Luarca
(74) *Attorney, Agent, or Firm* — Benoit & Cote Inc.; Mathieu Miron

(57) ABSTRACT

The present document describes a facial interface comprising a flexible face contact layer configured to cover a user's face; and a nasal layer configured to sealably cover an external nose region of said user. The flexible face contact layer and nasal layer provide fluid circulation of air through said user's nostrils.

17 Claims, 11 Drawing Sheets

(56) References Cited

U.S. PATENT DOCUMENTS

| | | | |
|---|---|---|---|
| 6,758,215 B2 * | 7/2004 | Begum | A41D 13/1161 |
| | | | 128/202.15 |
| 8,291,906 B2 | 10/2012 | Kooij et al. | |
| 2009/0223518 A1 * | 9/2009 | Kwok | A61M 16/0633 |
| | | | 128/205.25 |
| 2011/0005524 A1 | 1/2011 | Veliss et al. | |
| 2012/0204881 A1 * | 8/2012 | Davidson | A61M 16/0683 |
| | | | 128/206.25 |
| 2015/0352307 A1 | 12/2015 | Rutan | |
| 2017/0258638 A1 * | 9/2017 | Wallis | A61F 9/026 |

FOREIGN PATENT DOCUMENTS

| | | |
|---|---|---|
| CN | 101954139 | 1/2011 |
| JP | 2011045661 A | 3/2011 |
| JP | 5818191 B1 | 11/2015 |
| WO | 2014120492 A1 | 8/2014 |

OTHER PUBLICATIONS

Extended European Search Report, dated Apr. 11, 2019, European Patent Application No. 17735783.7, 5 pages.

* cited by examiner

FACIAL INTERFACE

CROSS-REFERENCE TO RELATED APPLICATIONS

This application is a US National Phase application under 35 USC § 371 of PCT/CA2017/050007, filed Jan. 5, 2017, which claims priority from and the benefit of U.S. Provisional Patent Application No. 62/275,526, filed Jan. 6, 2016, the specifications of which are hereby incorporated by reference in their entireties.

BACKGROUND

(a) Field

The subject matter disclosed generally relates to facial interfaces. More particularly, the subject matter relates to a facial interface comprising a flexible face contact layer configured to cover a user's face; and a nasal layer, configured to sealably cover an external nose region of the user. The flexible face contact layer and the nasal layer provide fluid circulation of air through said user's nostrils.

(b) Related Prior Art

Continuous positive airway pressure (CPAP) is the use of positive pressure to maintain a continuous level of positive airway pressure to prevent collapse of airways in users prone to sleep apnea. CPAP at home utilizes machines specifically designed to deliver a constant or variable flow or pressure.

CPAP treatment involves a CPAP machine, with an air compressor that is a pressure flow generating device, a mask or other device that fits over a user's nose or nose and mouth (straps keep the mask in place while worn) and a tube that connects the mask to the CPAP machine. When the CPAP is turned on and the mask is in place on the user, air flows under pressure through the tube into the mask, allowing air to flow under pressure into the patient's airway. The pressured airflow is designed to reduce or eliminate airway collapse often occurring in the upper airway, such that air flow will be unimpeded into the user's lungs allowing for oxygen transport into the user's circulation and removal of carbon dioxide through exhalation ports of the mask. Some CPAP machines have other features as well, such as heated humidifiers. CPAP machines and masks come in a variety of shapes and sizes, with the majority being small and lightweight.

The CPAP masks are typically a nasal mask (covering the whole nose), facial mask (nasal/oral) or nasal pillow mask (directly on the nostrils) which fit on the face of a patient to interface the ventilator or pressure support system with the airway of the patient so that a flow of breathing gas can be delivered from the pressure flow generating device to the airway of the patient. Straps on the mask are designed to maintain such masks on the face of a patient to ensure best positioning of the mask. In particular, there is headgear generally having upper and lower straps, each having opposite ends threaded through connecting elements provided on the opposite lower sides and top of a mask. Typically, patient CPAP devices include a mask shell having a cushion attached to the shell that contacts the facial skin of the patient. The mask shell and cushion are held in place by the headgear with straps that wrap around the head of the patient. The mask and headgear form the patient device assembly. A typical headgear includes flexible, adjustable straps that extend from the mask to attach the mask to the patient. In some circumstances, the adjustable straps extend from the mask and contact the facial skin.

Because such masks are typically worn for an extended period of time, a variety of concerns must be taken into consideration. For example, in providing CPAP to treat sleep apnea, the patient normally wears the patient CPAP device all night long while he or she sleeps. One concern in such a situation is that the patient CPAP device is as comfortable as possible; otherwise, the patient may avoid wearing the interface device, defeating the purpose of the prescribed pressure support therapy. Indeed, CPAP masks often results in patient discomfort caused by a persistent sensation of leaks of air on the face of the patient, irritations, rashes, and facial sores and other marks caused by prolonged wear of the mask.

It is also important that the CPAP device provide a tight enough seal against a patient's face without discomfort. CPAP apparatuses are designed to accept a certain air leakage rate without compromising therapy, by maintaining a prescribed air pressure. However, air leakage being extremely unpleasant for the patients and causes dryness of the eye, causing the patients to tighten the mask, to obtain a better seal. A problem thus arises when the mask is compressed against the patient's face in order for the mask to maintain a seal without any undue gas leaks around the periphery of the mask. This can cause facial sores and unsightly pressure marks upon arising after sleeping with the mask.

It is well known to deliver aerosolized medicaments, or therapeutic gasses such as oxygen to a patient via various devices, including nebulizers and aerosol dispensing devices, such as pressurized Metered Dose Inhalers (PMDI's), or medical ventilators, in order to treat various conditions and diseases, including but not limited to various respiratory conditions and diseases such as asthma. Such devices frequently use a face mask for administrations of aerosolized medicaments or therapeutic gasses. These masks may cause facial sores and unsightly pressure marks.

Therefore, there exists a need in the art for a device and method of use that ensures that the CPAP mask maintains connection between face and mask, without interfering the flow of air from the mask, and provides comfort for user to wear the mask, muffles and protects against feeling of air leaking on skin from the mask, reduces or eliminates wounds and marks on the skin and thus promotes adherence to the therapy.

Therefore, there exists a need in the art for a device and method of use that ensures that the face mask maintains connection between face and mask, without interfering the flow of aerosolized medicaments or therapeutic gasses from the mask, and provides comfort for user to wear the mask, muffles and protects against feeling of air leaking on skin from aerosolized medicaments or therapeutic gasses, reduces or eliminates wounds and marks on the skin and thus improves comfort of wearing such respiratory mask by the patient.

It is therefore a primary object, feature, and/or advantage of the present invention to overcome deficiencies in the art.

SUMMARY

According to an embodiment, there is provided a facial interface comprising:
  a flexible face contact layer configured to cover a user's face; and
  a nasal layer configured to sealably cover an external nose region of the user, wherein the flexible face contact layer and the nasal layer provide fluid circulation of air through the user's nostrils.

The flexible face contact layer may be further configured to cover a neck region, a forehead, a temporal region, a cheek region, a jaw region, a chin region, of a user's face, or combinations thereof.

The flexible face contact layer may be further configured to cover the external nose region.

The flexible face contact layer may be further configured for a contact free overlay of an ocular region of a user's face.

The flexible face contact layer may comprise a slot and a flap, wherein the flap may be configured for a contact free overlay of an ocular region of a user's face and may be foldable away from the ocular region, to allow the user to see through the interface.

The flexible face contact layer may be further configured to cover the external nose region of the user and provide fluid circulation of air through the user's nostrils.

The flexible face contact layer and/or the nasal layer may comprise an opening over a nasal tip of the user.

The flexible face contact layer and/or the nasal layer may be opened over the nostrils of the user.

The flexible face contact layer and/or the nasal layer may further comprise a breathable overlay over the nostrils of the user.

The flexible face contact layer and/or the nasal layer may be configured to cover a base of the eye area.

The flexible face contact layer and/or the nasal layer may be configured to cover a bridge of the nose, around the nose and nostrils, or a combination thereof.

The flexible face contact layer and/or the nasal layer may further comprise a sub-nasal tab for coverage of a contour of the nose and nostrils.

The sub-nasal tab may comprise a pair of sub-nasal tab on each side of the nostrils, without joining under the nose.

The sub-nasal tab may comprise a single sub-nasal tab joining under the nose.

The nasal layer may be configured to provide tone to the facial interface.

The nasal layer may be configured to provide padding to the facial interface.

The nasal layer may be further configured for a contact free overlay an ocular region of a user's face.

The nasal layer may be laminated over the flexible face contact layer.

The facial interface may further comprise a flexible external layer, contacting the flexible face contact layer and/or the nasal layer, configured to modulate thickness of the facial interface.

The flexible external layer may be further configured to cover an external nose region of the user and provide fluid circulation of air through the user's nostrils.

The facial interface may further comprise a nasal padding layer, to provide padding to say nasal layer, and may be configured to cover an external nose region of the user and provide fluid circulation of air through the user's nostrils.

The facial interface may further comprise a cervical wing, configured to cover a neck region.

The cervical wing may be a pair of cervical wing configured to cover both sides of a neck region.

The facial interface may further comprise an oricular clearance, configured to provide clearance between ears of the user and the facial interface.

The facial interface may further comprise a grip layer to provide adherence and prevent slippage of an overlaid mask from the facial interface.

The grip layer may be configured to cover the external nose region, a neck region, a temporal region, a forehead region, and combinations thereof.

The facial interface may further comprise means to maintain the facial interface in place on a user's head.

The means to maintain the facial interface in place on a user's head comprises an ear strap, a head strap, and an adherent material.

In the facial interface of the present invention, any one of the flexible face contact layer, the nasal layer, the flexible external layer, or the nasal padding layer may be configured as having a thickness tapering off toward an outline of the facial interface, to avoid marking of the user's skin from use of the facial interface.

The facial interface may be configured as having a thickness tapering off toward an outline thereof, to avoid marking of the user's skin from use of the facial interface.

The flexible face contact layer may be made from a breathable fabric.

The nasal layer may be made from a non-breathable material.

The flexible external layer may be made from a breathable fabric.

The flexible face contact layer may be made from a woven, non-woven, or knitted fabric, or combinations thereof.

The facial interface may be for use with a positive airway pressure device.

According to another embodiment, there is provided a method for the treatment of sleep apnea in a patient in need thereof, comprising the step of contacting a patient's face with a facial interface according to the present invention, prior to treatment with a positive airway pressure device.

According to another embodiment, there is provided a method for the treatment of sleep apnea in a patient in need thereof, comprising the step of treating the patient with a positive airway pressure device and a facial interface according to the present invention.

According to another embodiment, there is provided a method for the administration of a therapeutic gas to a patient in need thereof, comprising the step of contacting a patient's face with a facial interface according to the present invention, prior to administration of the therapeutic gas or substance with a gas administration device.

According to another embodiment, there is provided a method for the administration of a therapeutic gas to a patient in need thereof, comprising the step of administering the therapeutic gas or substance to the patient with a gas administration device and a facial interface according to the present invention.

According to another embodiment, there is provided a use of the facial interface according to the present invention, and a positive airway pressure device, for the treatment of sleep apnea in a patient in need thereof.

According to another embodiment, there is provided a use of the facial interface according to the present invention, and a gas administration device, for administration of a therapeutic gas or substance to a patient in need thereof.

According to another embodiment, there is provided a facial interface according to the present invention for use in the treatment of sleep apnea in a patient in need thereof.

According to another embodiment, there is provided a facial interface according to the present invention for use in the administration of a therapeutic gas or substance to a patient in need thereof.

The following terms are defined below.

The term "face" is intended to mean the front part of a person's head from the forehead to the chin.

The terms "nose" and "nasal region" is intended to mean the part projecting above the mouth on the face of a subject, containing nasion, dorsum, the lobule (including the supra-tip area and tip), the columella, the nostrils, the alar groove, nasolabial fold and angle, and is used for breathing and smelling.

The terms "opening" or "open" is intended to mean that the region over which the so called opening or openness is found is not covered by any fabric or material. The element of the facial interface of the present invention may simply lack any region covering the face of the user in this region, or it may comprise a hole to leave the face of the user in this region uncovered.

Features and advantages of the subject matter hereof will become more apparent in light of the following detailed description of selected embodiments, as illustrated in the accompanying figures. As will be realized, the subject matter disclosed and claimed is capable of modifications in various respects, all without departing from the scope of the claims. Accordingly, the drawings and the description are to be regarded as illustrative in nature and not as restrictive and the full scope of the subject matter is set forth in the claims.

BRIEF DESCRIPTION OF THE DRAWINGS

Further features and advantages of the present disclosure will become apparent from the following detailed description, taken in combination with the appended drawings, in which.

It will be noted that throughout the appended drawings, like features are identified by like reference numerals.

DETAILED DESCRIPTION

Figure 1:
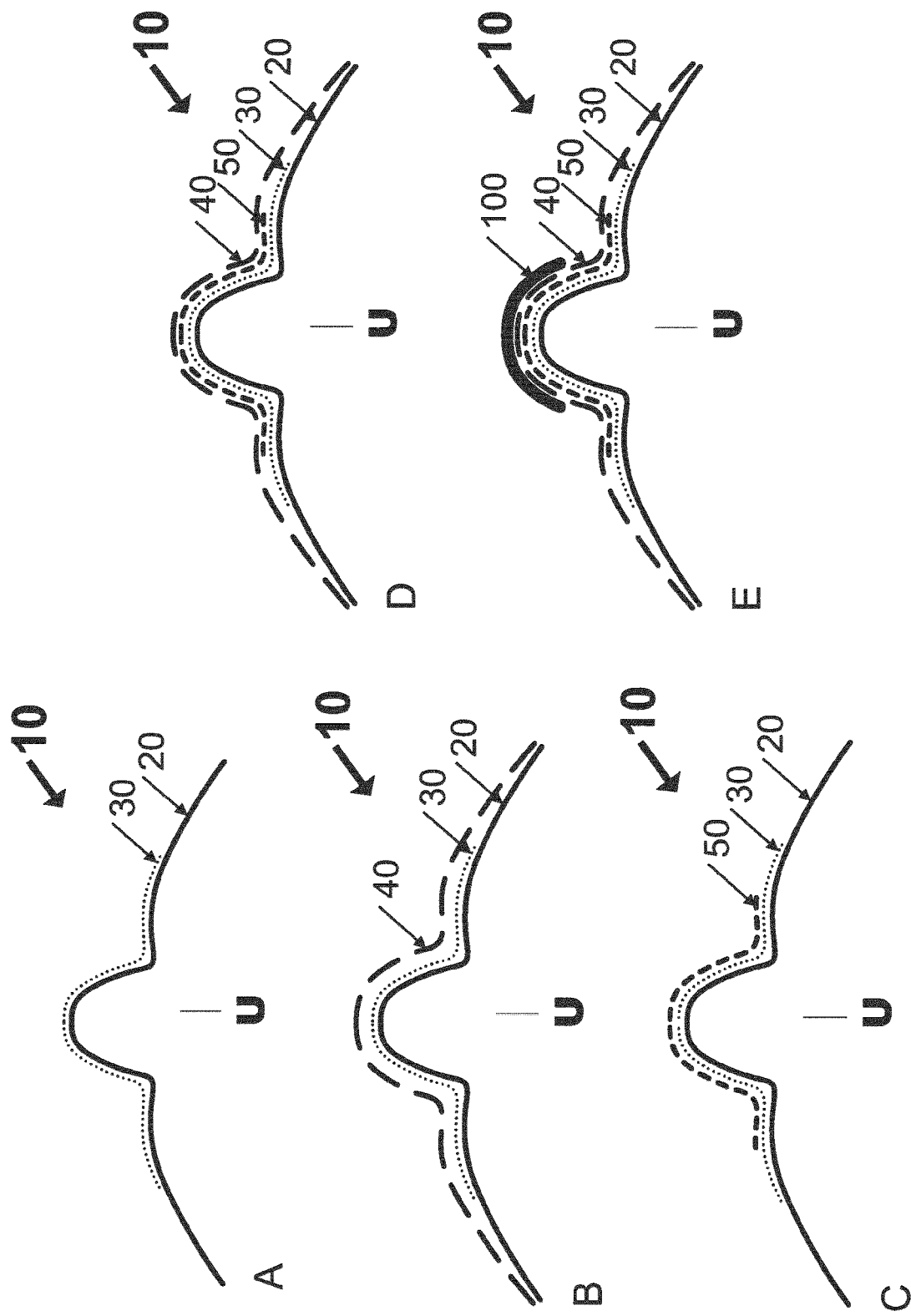
FIGS. 1A-E illustrate top view of a facial interface overlaid on a user's face, according to an embodiment of the present invention.
Figure 2:
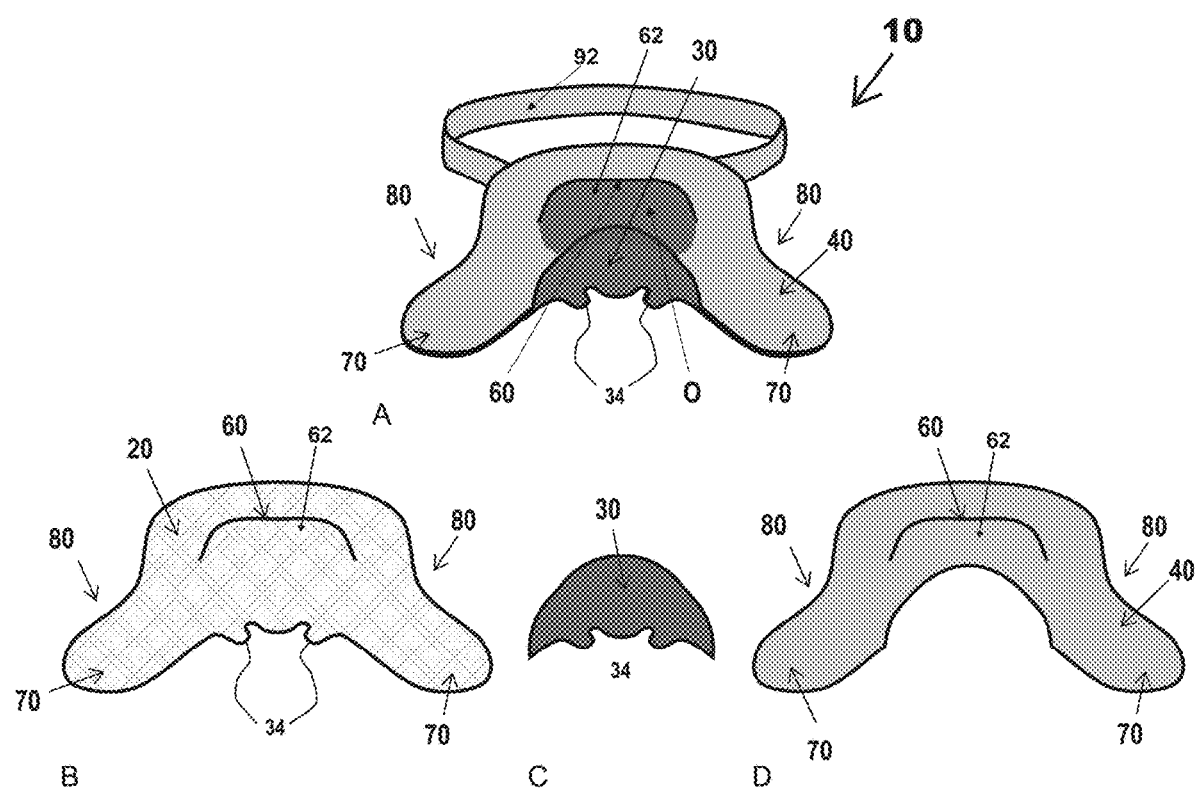
FIGS. 2A-D illustrate front view of a facial interface according to an embodiment of the present invention. (A) illustrates the assembled interface, (B) shows the flexible face contact layer, (C) the nasal layer, and (D) the flexible external layer.
Figure 3:
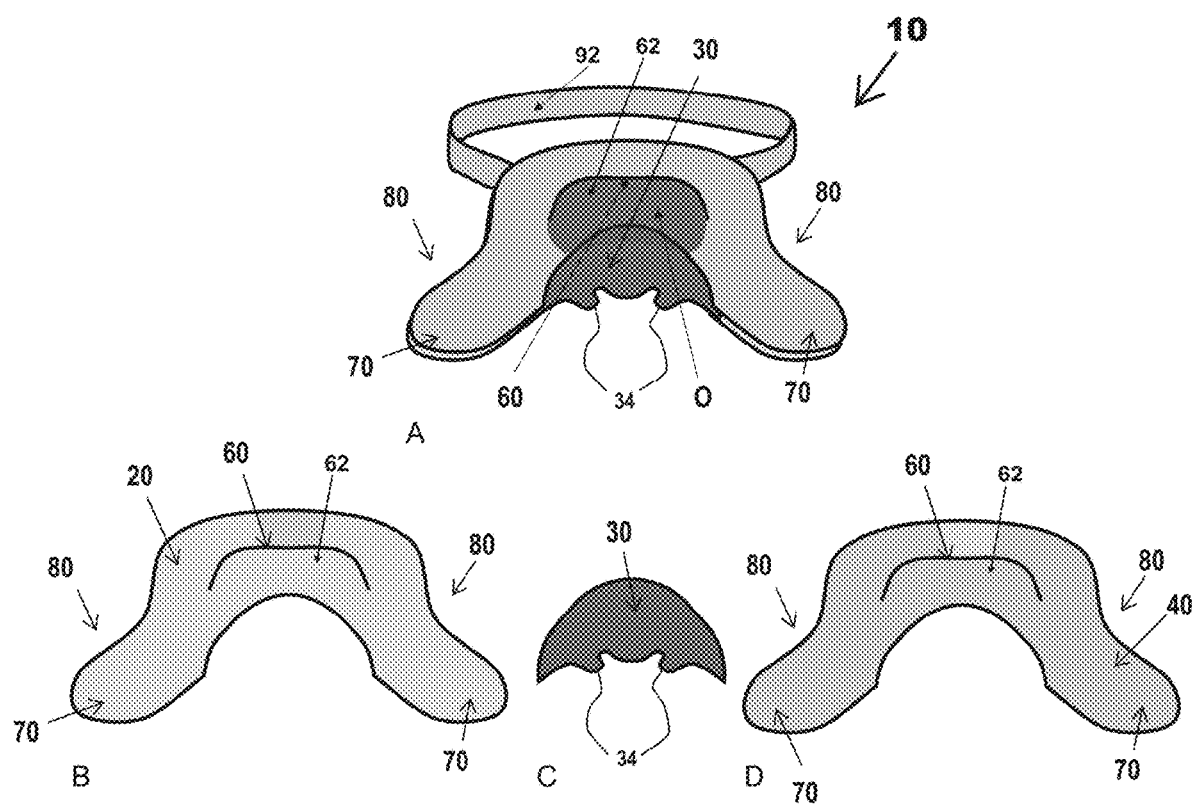
FIGS. 3A-D illustrate front view of a facial interface according to an embodiment of the present invention. (A) illustrates the assembled interface, (B) shows the flexible face contact layer, (C) the nasal layer, and (D) the flexible external layer.
Figure 4:
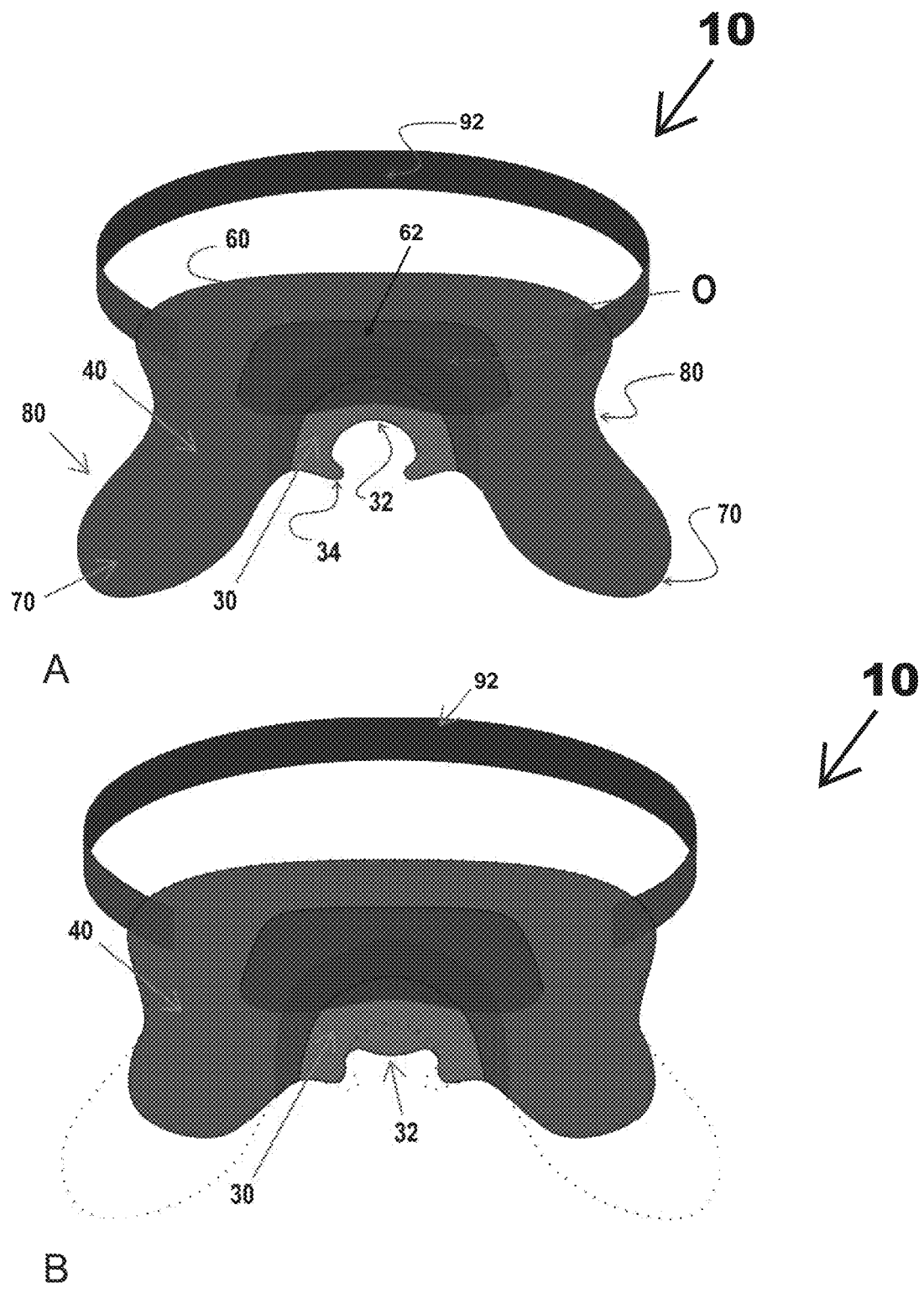
FIGS. 4A-B illustrate front views of a facial interface according to embodiments of the present invention.
Figure 5:
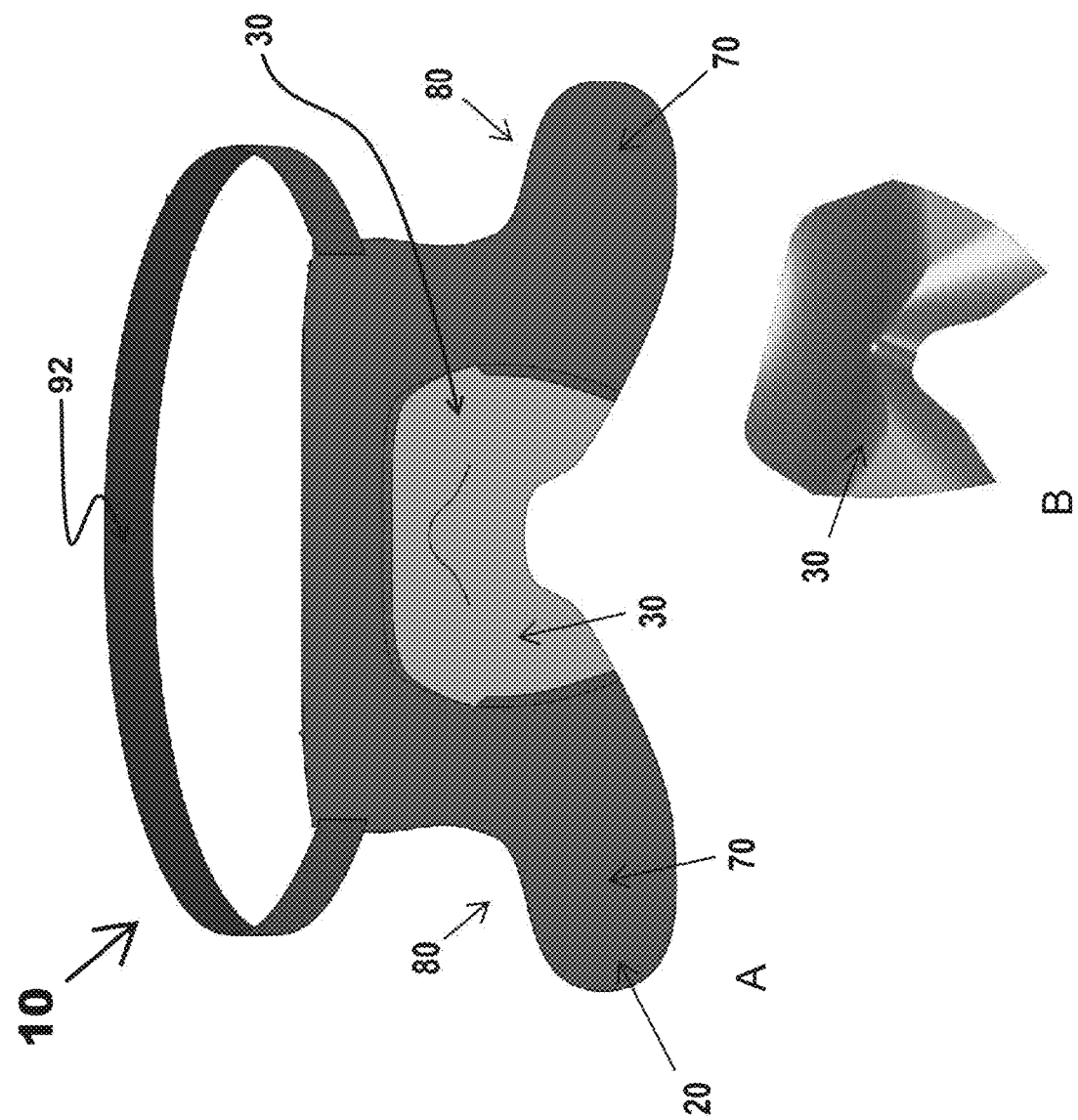
FIGS. 5A-B illustrate front views of a facial interface according to embodiments of the present invention. (A) illustrates the assembled interface, and (B) a thermoformed nasal layer 30 which is also configured to protect against air leaks the ocular region of a user's face.

Referring now to the drawings, and more particularly to FIGS. 1 to 5 and 7, in embodiments there is disclosed a facial interface 10 comprising a flexible face contact layer 20, which is configured to cover a user's face. The facial interface 10 also comprises a nasal layer 30, which is configured to sealably cover an external nose region of the user. Each of the flexible face contact layer 20 and the nasal layer 30 provide fluid circulation of air through the user's nostrils. Now referring to FIGS. 7A-D, which illustrate embodiment where the flexible face contact layer 20 covers (A) the forehead, temporal region, cheek region, neck region, jaw chin regions, the nose and the eyes; (B) the forehead, temporal region, cheek region, neck region, the nose and the eyes; (C) temporal region, upper cheek region, the nose and the eyes; and (D) cheek region and the nose only. Preferably, the facial interface 10 is for use with a positive airway pressure device, but may be used in any other application where it may be suitable.

FIGS. 1A-E illustrate different overlay of layer according to embodiments of the present invention. In embodiments, the flexible face contact layer 20 may be made from a thin layer of flexible fabric such as polyester, nylon, and/or cotton, or combinations thereof (which may be woven, knitted, or non-woven fabric), and that is suitable to be thermoformed if desired. In an embodiment, the fabric of the flexible face contact layer 20 is a breathable fabric, and provides relief from the discomfort normally felt by the plastic mask shell when the facial interface 10 of the present invention is present.

Figure 6:
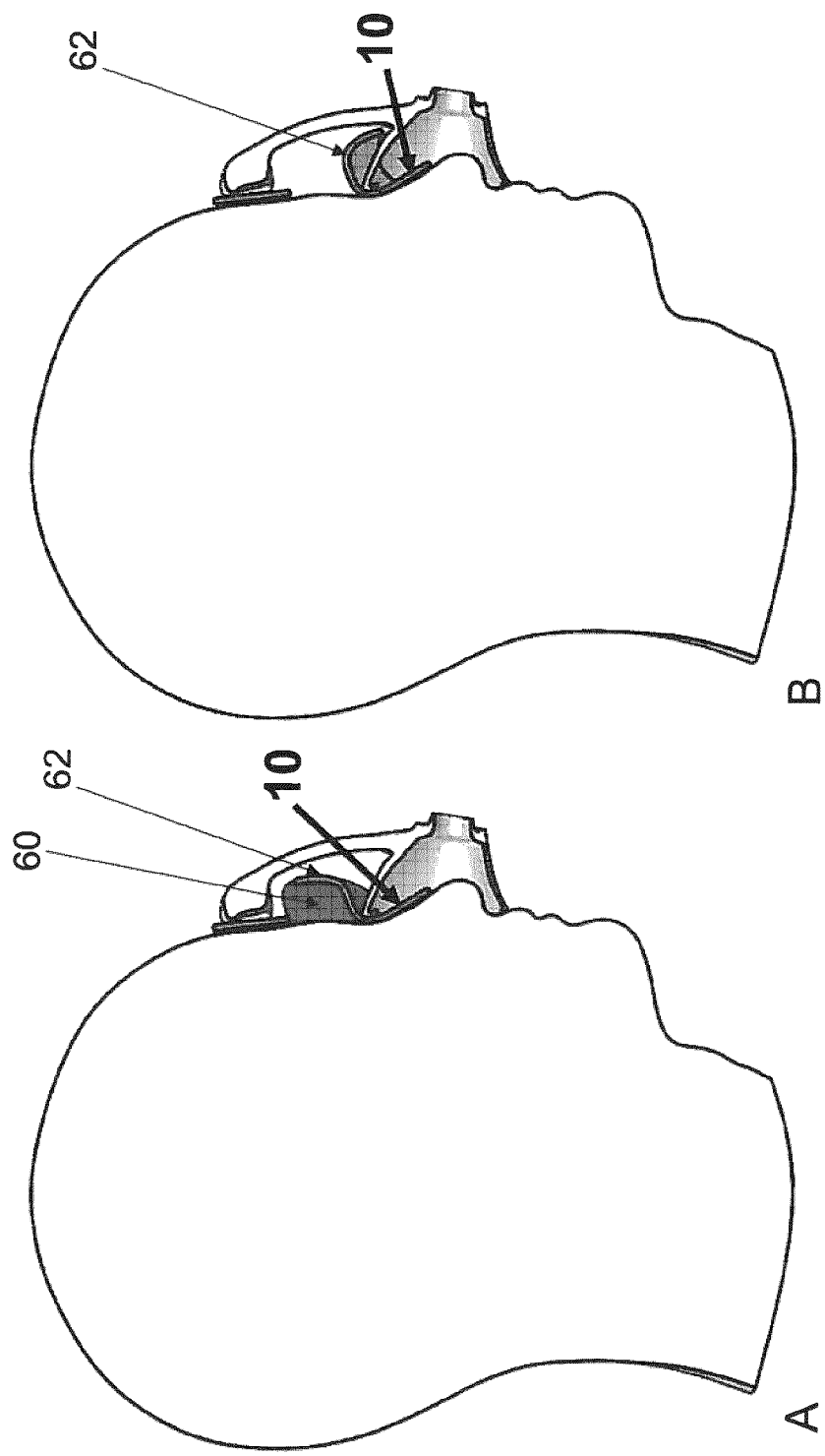
FIGS. 6A-B illustrate side views of a facial interface according to embodiments of the present invention, connected to a CPAP mask. (A) illustrates the interface of the present invention with a facial interface 10 with the material overlaying the eye region, and (B) illustrates the interface of the present invention with a facial interface 10 lowered and not covering the eye region.
Figure 7:
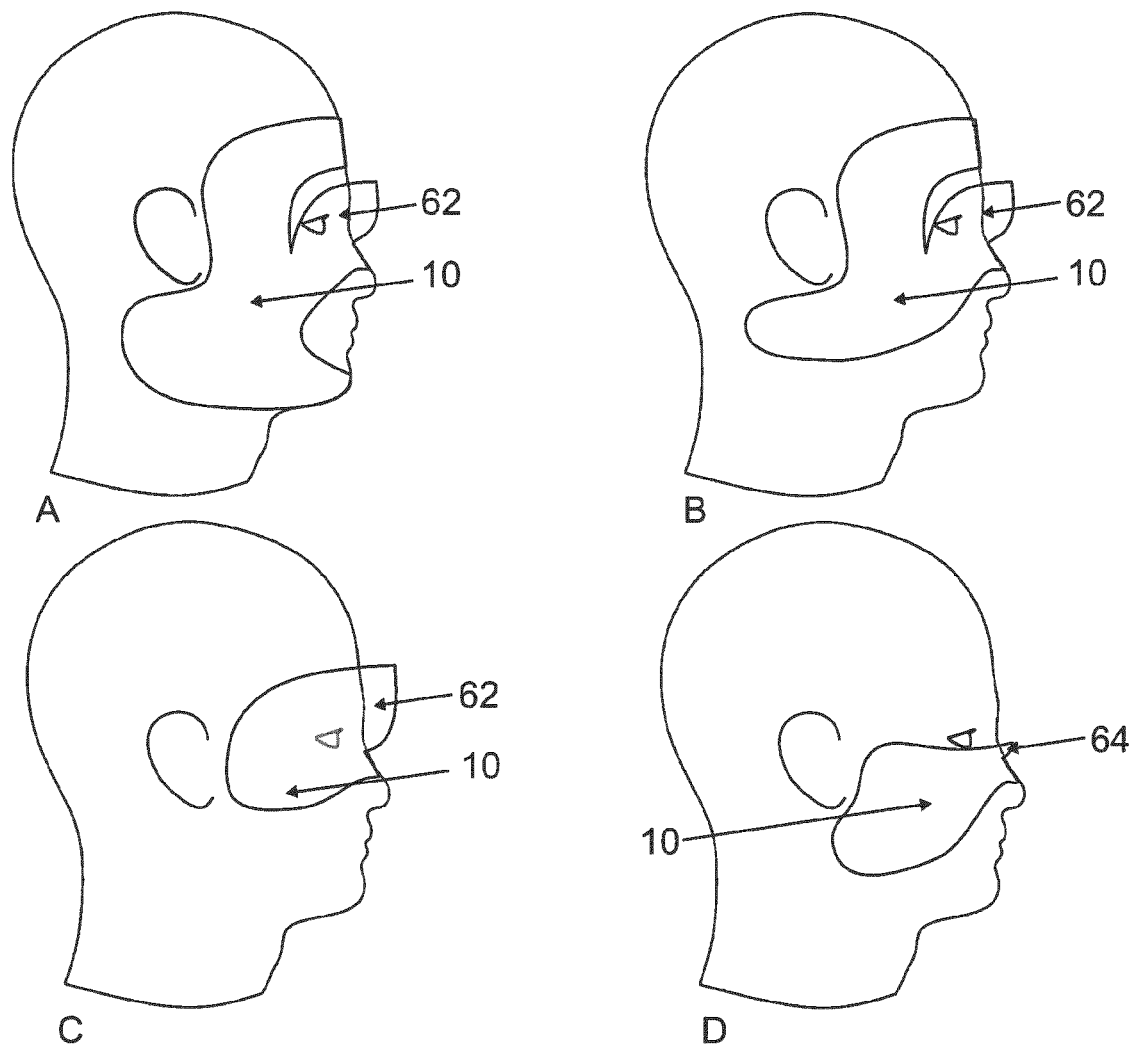
FIGS. 7A-D illustrate side views of facial interfaces according to embodiments of the present invention where the facial interface 10 contacts (A) the forehead, temporal region, cheek region, neck region, jaw, chin regions and the nose; (B) the forehead, temporal region, cheek region, neck region and the nose; (C) temporal region, upper cheek region and the nose; and (D) cheek region and the nose only.

In embodiments, the flexible face contact layer 20 prevents air leaks from the CPAP mask from blowing on the facial skin, including the patient's forehead, a temporal region and a cheek region, neck region, jaw and chin regions, and particularly the eyes. Indeed, in embodiments, the flexible face contact layer 20 may be further configured to overlay an ocular region (0) of a user's face, such region shown in FIGS. 2-4. In one such embodiment, the flexible face contact layer 20 covers the ocular region (0), but does not directly contact eyes and eyelids of the ocular region (0). In another embodiment, the flexible face contact layer 20 covers the ocular region (0), and may be formed such that a three-dimensional shaped is provided to the region covering the ocular region, such that the fabric does not directly contact the ocular region. The flexible face contact layer 20 has sufficient space (i.e. clearance) to provide a well aerated area between the flexible face contact layer 20 and the eyes of the patient, such that on the one hand they are well shielded from the air leaks from the CPAP mask, and on the other hand allow the eyes to breath, avoiding the sensation of warmth and moistness created from poor air circulation around the eyes. Now referring to FIGS. 6 and 7A-C, in another embodiment, the region of the facial interface 10 covering the ocular region may also comprise a slot 60, and a flap 62 that may be lowered by the user as deemed necessary, for example, when the patient desires to see around him or her. FIGS. 6A and 7A-C show the facial interface 10 overlaying the eyes and yet providing clearance with the eyes, while FIG. 6B shows the facial interface 10 having been lowered by lowering the flap 62, and FIG. 7D shows only an air deflector 64 not covering the eye region.

According to another embodiment, the facial interface 10 may be further configured to cover an external nose region of the user and provide fluid circulation of air through the user's nostrils. That is, the facial interface 10 may be configured in such a fashion that the forehead, temporal region and cheek region and nasal region are all covered.

In embodiments, the nasal layer 30 is configured to provide seal to the flexible face contact layer 20 in the external nose region of the user and afford fluid circulation of air through the user's nostrils. In embodiments, the nasal layer 30 is formed such that it is imparted a "nose" shape that may espouse the shape of a user's nose. According to an embodiment, the nasal layer 30 is thermoformed in the appropriate shape. The shape imparted to the nasal layer 30 using an appropriate material selection, result in the seal of the nose region of the flexible face contact layer 20. In embodiments, the nasal layer 30 may also cover the bottom/base of the eye area, including the infraorbital region, particularly where there is bone underneath the skin. In embodiments, the nasal layer 30 may also cover the bridge of the nose, around the nose and nostrils. Suitable material include but are not limited to polymeric material that may form thin layers, remain supple and flexible, and that may be formed or molded (e.g. when warmed or heated). Suitable polymeric materials include but are not limited to copolymers of ethylene and vinyl acetates. Preferably, the polymeric material is a thermoformable polymeric material. In particular embodiments, the suitable material used for the nasal layer 30 may be non-breathable material, to form the best seal possible.

The nasal layer 30 may be, in an embodiment, joined to the flexible face contact layer 20 through assembly with ultrasound, sewing, or pressing, or by thermoforming. Now referring to FIG. 3, in particular 3B, in an embodiment, the nasal layer 30 may be joined to a flexible face contact layer 20 which does not possess a region to cover the external nose region of the user. In this fashion, the nasal layer 30 covers directly the nose. Now referring to FIG. 2, in particular FIG. 2B, in yet another embodiment, the nasal layer 30 may be joined to a flexible face contact layer 20 which does possess a region to cover the external nose region of the user. In this fashion, the nasal layer 30 is laminated over the flexible face contact layer 20 which covers directly the nose. In embodiments, the nasal layer 30 may also cover the bottom/base of the eye area, including the infraorbital region, particularly where there is bone underneath the skin. In embodiments, the nasal layer 30 may also cover the bridge of the nose, around the nose and nostrils.

In embodiments, the nasal layer 30 may create a seal between the CPAP mask and the skin, so as to prevent the air projected on the nose through the nozzle from penetrating under the interface to the base of the eyes. The nose is accustomed to feel the air, but not the eyes. This gives rise to profound discomfort. In embodiments, nasal layer 30 may be configured such that it provides fluid circulation of air through the user's nostrils. That is, flow of air will not be impeded by the fabric or material of the nasal layer 30. This may be achieved in a number of suitable ways. Now referring to FIGS. 4A-B, according to an embodiment, the nasal layer 30 may be opened (e.g. opening 32) over a nasal tip of the user, leaving space for air to flow. In another embodiment, the nasal layer 30 may be opened (e.g. comprise an opening) over the nostrils of the user. In an embodiment, the nasal layer 30 may be opened (e.g. comprise an opening) over both the nasal tip of the user and the nostrils. According to yet another embodiment, the nasal layer 30 may comprise an overlay over the tip and nostrils that may be made of a material that does not impede the fluid circulation of air through the user's nostrils, such as a breathable fabric or a mesh or holes in the fabric covering the nostrils.

Figure 8:
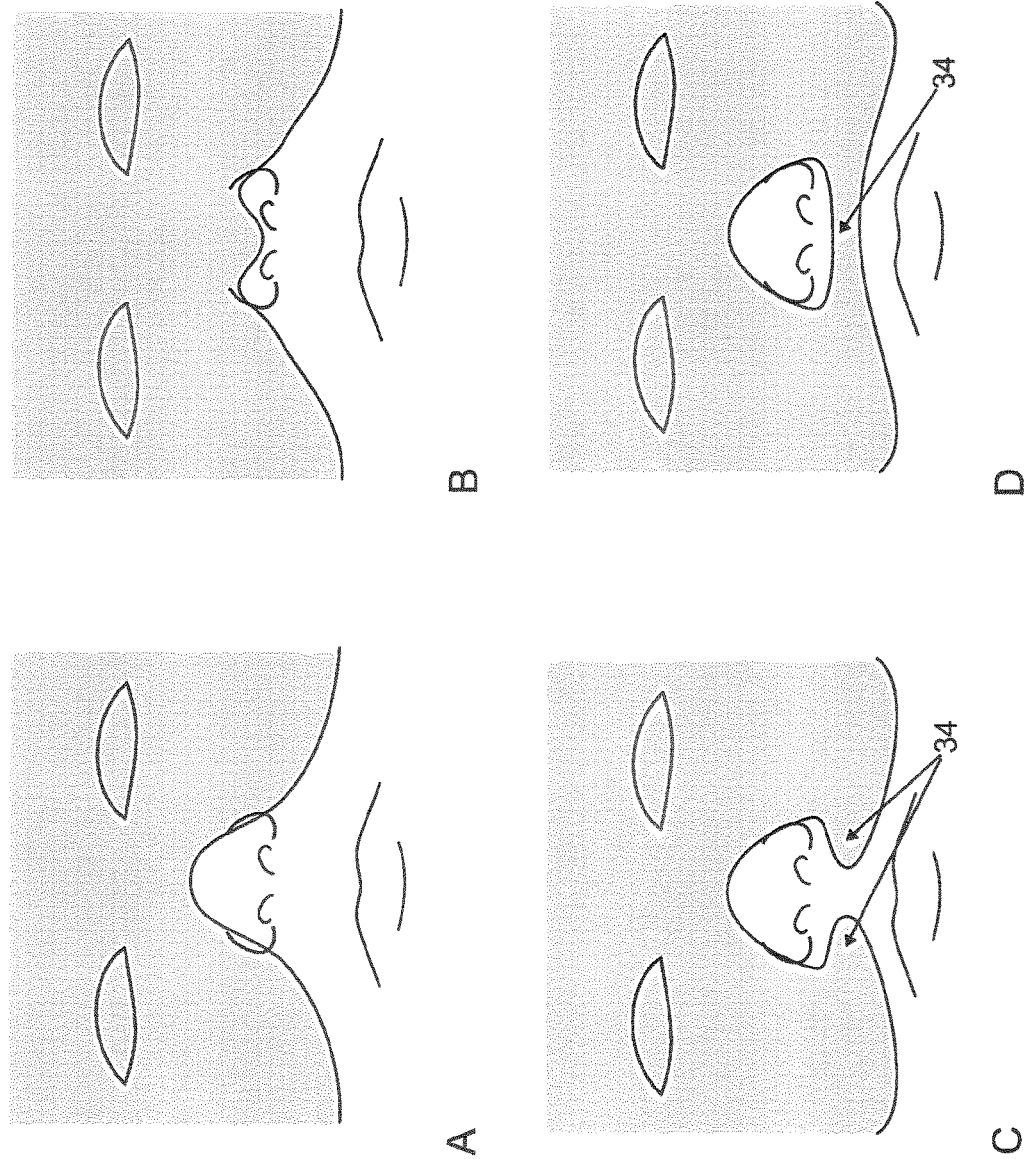
FIGS. 8A-D illustrate front views of facial interfaces according to embodiments of the present invention contacting (A) the nose, excluding the tip; (B) the nose, including the tip; (C) the nose and includes a pair of sub-nasal tab 34; and (D) the nose and includes a continuous sub-nasal tab 34 under the nose.

Now referring to FIGS. 2-4 and 8C-D, according to another embodiment, the nasal layer 30 may further comprise sub-nasal tabs 34. The sub-nasal tabs 34 ensures adequate coverage of the contour of the nose and nostrils without joining under the nose (FIG. 8C). The sub-nasal tabs 34 help create a seal between the skin and the facial interface 10 around this region of the face. In embodiments, the sub-nasal tabs 34 are shaped according to a patient's face in order to provide optimal seal with the CPAP mask, and may therefore be shorter or longer as may be needed. In one embodiment, the sub-nasal tabs 34 bypass the nose, without obstructing the nostrils, to continue below the nose. In embodiment, the sub-nasal tabs may join to from a continuous sub-nasal strip under the nose (FIG. 8D).

According to other embodiments, the nasal layer 30 may be configured to provide tone as well as padding to the nasal layer 30. As used herein, the term tone is intended to mean that the nasal layer 30 provides a certain firmness and structure to the facial interface 10, while remaining flexible so as to espouse the nose of the user and provide the desired function. The term padding is intended to mean that either the material used for fabricating the nasal layer 30 is sufficiently soft and/or configured (e.g. by increasing thickness of the material, weaving or forming the material in three dimensions, etc.) to provides cushioning, structure and protection and/or that a padding material (e.g. stuffing material or fabric, trapping air in a material pocket, etc.) is inserted in the material used for fabricating the layer(s) to provide such padding.

According to other embodiments, the nasal layer 30 is configured to provide tone to the facial interface 10. As used herein, the term tone is intended to mean that the nasal layer 30 provides a certain firmness and structure to the facial interface 10, while remaining flexible so as to espouse the face of the user and provide the desired function. In embodiment, a laminated polymer can be molded into the desired shape, which it will keep. The shape is intended to guide the placement of the facial interface 10 in the proper position on the face, at the time of use. Yet, the shape remains sufficiently flexible to conform to differently shaped nose.

Now referring to FIGS. 5A and B, in another embodiment, the nasal layer 30 may be configured to overlay an ocular region of a user's face. In one such embodiment, the nasal layer 30 covers the user's eyes and overlays the ocular region. In yet another embodiment, the nasal layer 30 covers the ocular region, and may be formed such that a three-dimensional shape is provided to the region covering the ocular region, such that the fabric does not directly cover the ocular region.

Now referring to FIGS. 1 to 4, according to another embodiment the facial interface 10 may further comprise a flexible external layer 40, which is covering the flexible face contact layer 20, and/or the nasal layer 30, and/or other layers present in the facial interface 10, such as the nasal padding layer 50. In effect, the flexible external layer 40 may be the top layer of the facial interface 10.

In yet another embodiment, the facial interface 10 may be provided to respiratory therapist (or other therapist) or other appropriately trained personnel, or users as an unformed interface, where the polymer part would be formable by respiratory therapist (or other therapist) or other appropriately trained personnel, or users to the shape of their nose. Thermoforming would be possible if the polymer is thermoformable at medium temperature (e.g. in hot water).

According to an embodiment, flexible external layer 40 may be further configured to cover the face the user and provide fluid circulation of air through the user's nostrils. That is, the flexible external layer 40 may be configured in such a fashion that it overlaps with the regions of the face contact layer 20 that cover the forehead, temporal region, cheek region, neck region, jaw region, chin region, the nasal region, and the eyes region. In yet another embodiment, the flexible external layer 40 may provide padding to the facial interface 10, by its internal composition. The term padding is intended to mean that either the material used for fabricating flexible external layer 40 is sufficiently soft and/or configured (e.g. by increasing thickness of the material, weaving or forming the material in three dimensions, etc.) to provide cushioning, structure and protection, and/or that a padding material (e.g. stuffing material or fabric, trapping air in a material pocket, etc.) is inserted in the material used for fabricating the layer(s) to provide such padding.

In embodiments, the flexible external layer 40 may be made from a thin layer of flexible fabric such as polyester, nylon, and/or cotton, or combinations thereof (which may be woven, knitted, or non-woven fabric), and that is suitable to be thermoformed if desired. In an embodiment, the fabric of the flexible face contact layer 20 may be made from a breathable fabric.

Now referring to FIGS. 1C and D, the present invention may also encompass embodiments comprising a nasal padding layer 50, contacting the nasal layer 30 to provide padding to and over the nasal layer 30, which is configured to cover an external nose region of the user and provide fluid circulation of air through the user's nostrils. The nasal padding layer 50 may be flexible.

Now referring to FIGS. 2-5, according to other embodiments, the facial interface 10 may also comprise cervical wings 70 that shield and protect the face and neck of the user from the different straps used to maintain the CPAP mask or apparatus in place, which would otherwise leave unwanted marks on the user's face after prolonged use of the CPAP apparatus.

According to another embodiment, the facial interface 10 may also comprise auricular clearances 80 configured to provide clearance between the ears of the user and the facial interface 10.

In embodiments, the facial interface 10 may also comprise a grip layer 100, to provide an adherent layer to allow an overlaid mask (e.g. such as a CPAP mask) to adhere to the facial interface 10, and prevent slippage. In embodiments, a grip layer 100 may be placed anywhere where the interface will contact an overlaid mask. For example, the grip layer 100 could be placed over the nose region (such as shown in FIG. 1E), as well as over the neck region, temporal region, forehead region, and combinations thereof. In other embodiments, the grip layer 100 could be placed over cervical wings 70.

Figure 9:
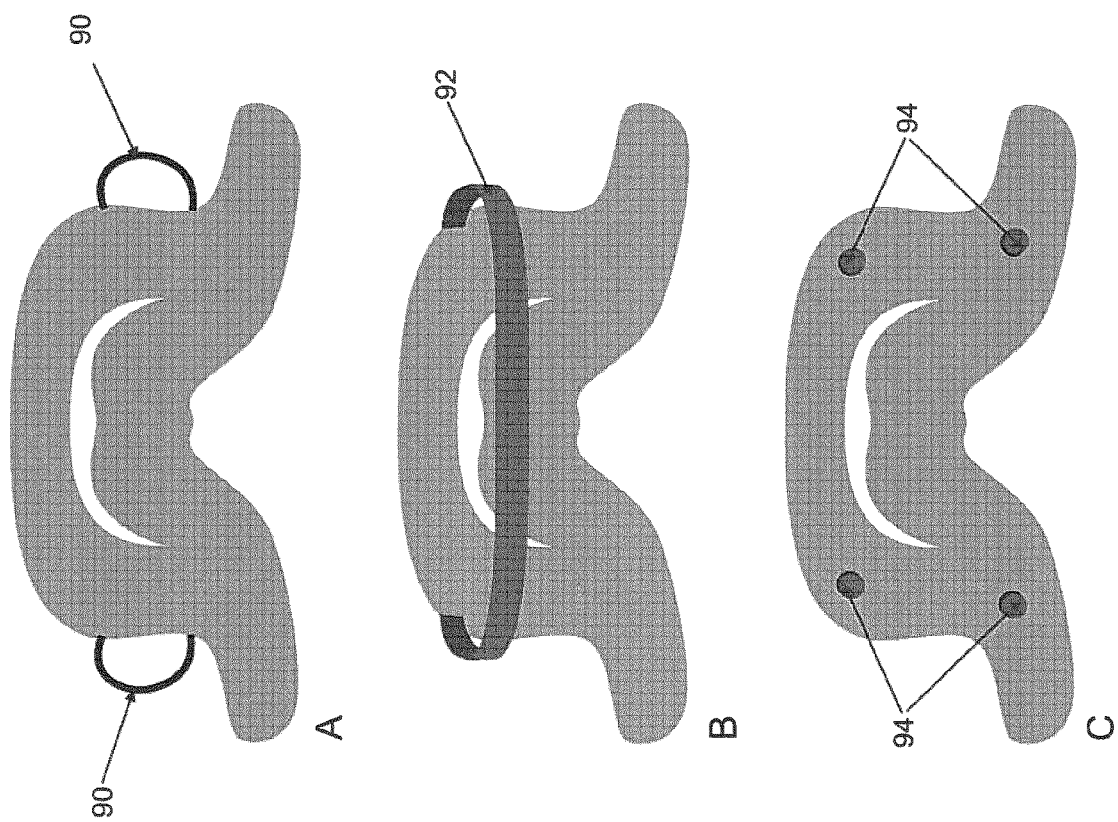
FIGS. 9A-C illustrate means to maintain the facial interface 10 in place on a user's head: (A) ear straps 90 (B) head strap 92, and (C) adherent material (e.g. dots or bands) 94.

According to another embodiment, the facial interface 10 may also comprise means to maintain the facial interface 10 in place on a user's head. Now referring to FIG. 9, for example, such may include (A) ear straps 90, (B) head strap 92, as well as (C) adherent material (e.g. dots or bands) 94, to maintain the facial interface 10 in place on a user's head. Head strap 92 are also shown in FIGS. 2-5.

Figure 11:
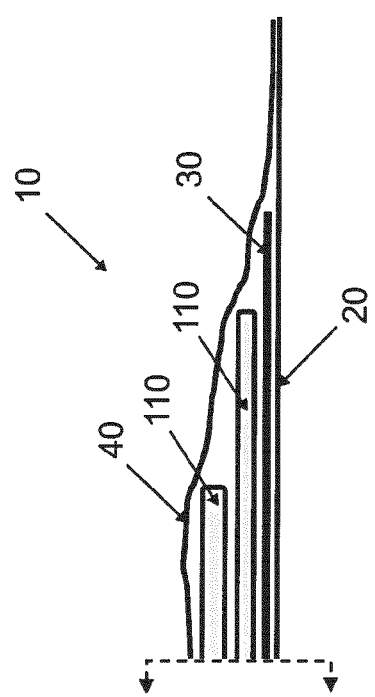
FIG. 11 illustrates a cross sectional view of a facial interface 10 according to an embodiment of the present invention.

In embodiments, each of the flexible face contact layer 20, nasal layer 30, flexible external layer 40, nasal padding layer 50 or the grip layer 100 may provide either closer contact with the skin of the user, or supplemental protection to the user by modulation of the thickness configuration of these layers. In a further embodiment, the thickness or thinness of independent sections of the facial interface 10, such as the nose region, neck region, a forehead, a temporal region, a jaw region, a chin region, ocular region, etc., and/or independent segments of the facial interface 10 such as the flap 62, sub-nasal tab 34, cervical wings 70, etc., may be varied for similar reasons. According to another embodiment, the thickness or thinness of each independent sections or segments may be varied in order to achieve increasing or decreasing thickness over the desired areas, such that for example, the thickness may be highest in the center of a given section or segment, and lowest at the periphery. In a similar yet distinct embodiment, thickness may taper off from the center of the section or segment to a reduced thickness at the outline. Now referring to FIG. 11, in an embodiment of the facial interface 10 of the present invention, the facial interface 10 is configured as having a thickness tapering off toward an outline thereof, to avoid marking of the user's skin from use. In these embodiments with relatively thinner thickness at the outline, the thinner thickness avoids marking of the skin of the user after prolonged use of the facial interface, from distribution of the pressure to areas of thicker thickness. FIG. 11 shows a cross sectional view of a facial interface 10 of the present invention, which comprises the flexible face contact layer 20, nasal layer 30, flexible external layer 40, as well as padding layers 110, having a thickness tapering off toward the outline thereof.

According to other embodiments, the thickness may be lowest in the center of a given section or segment, and highest at the periphery. In a similar yet distinct embodiment, thickness may taper off from the outline of the section or segment to a reduced thickness at the center.

According to an embodiment, the thickness of each sections or segments discussed above may be varied with either increased thickness of material of the sections or segments, or through added padding, as discussed above, (e.g. by increasing thickness of the material, weaving or forming the material in 3 dimension, or having additional layers, etc.), by providing cushioning, structure and protection to a user's nose and/or a padding material (e.g. stuffing material or fabric, trapping air in a material pocket, etc.).

Figure 10:
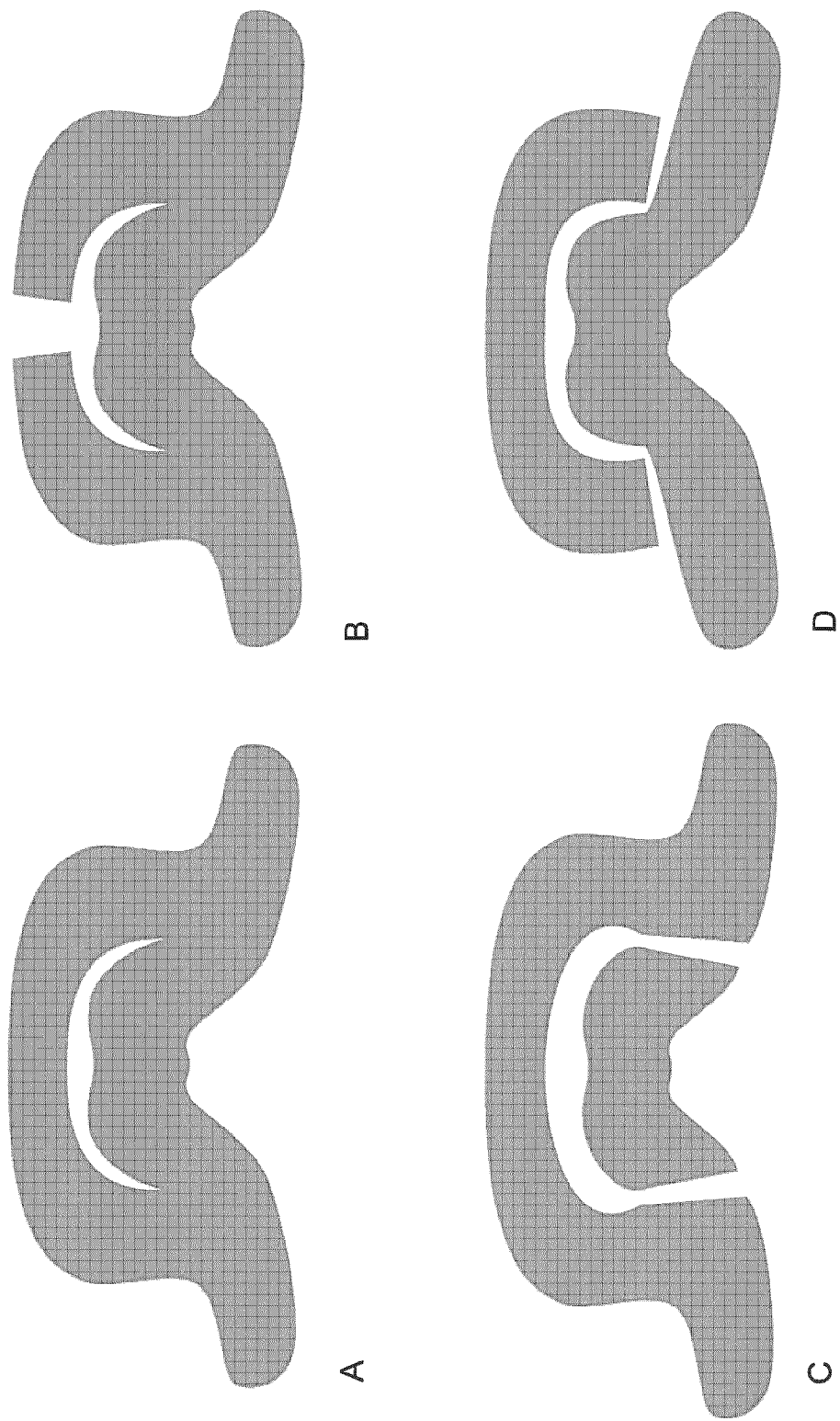
FIGS. 10A-D illustrate front view of different ways in which segments of different sections used in the facial interface of the present invention could be assembled.

The facial interface 10 of the present invention may be prepared from a number of laminated and/or joined layer of fabric and/or polymeric material. For example, a sealing layer made of film of polymeric material (e.g. the nasal layer 30) may be joined or fused to the underlying breathable fabric layer (e.g. the flexible face contact layer 20) through known techniques such as lamination in cold male-female molds, thermoforming in hot male-female molds, fusion of the fibers/polymeric materials by ultrasound in male-female molds, sewing, radio-frequency glue bonding, vacuum forming, die cutting, heat die cutting, etc. Now referring to FIGS. 10 A-D, the assembly may also be obtained by combining distinct sections with one another to achieve the facial interface 10.

In another embodiment, a sealing polymeric material coating layer (e.g. the nasal layer 30) can be overlaid to the underlying fabric layer (e.g. the flexible face contact layer 20) through known techniques of thermoforming in hot male-female molds after serigraphic printing of the coating layer.

A preferred method may be thermoforming, where the materials and/or fabric of the nasal layer 30 may resists to the temperature necessary for assembly with the other layers of the facial interface 10.

In embodiments of the present invention, the different overlay methods used to produce the facial interface 10 of the present invention will use any suitable materials and methods that maintain the seal with the user's nose, while at the same time maintain the flexibility, the breathability, suppleness and thinness of the facial interface 10. Non-limiting examples include but are not limited to polyurethanes, polyesters, nylons, ethyl vinyl acetates (EVA).

In another embodiment, there is disclosed a method of treating sleep apnea in a patient in need thereof, comprising the step of contacting a patient's face with a facial interface 10 of the present invention prior to treatment with a positive airway pressure device.

In another embodiment, there is disclosed a method of treating sleep apnea in a patient in need thereof, comprising the step of treating the patient with a positive airway pressure device and a facial interface 10 according to the present invention.

In another embodiment, there is disclosed a use of the facial interface 10 according to the present invention, and a positive airway pressure device, for the treatment of sleep apnea in a patient in need thereof.

In another embodiment, there is disclosed a facial interface 10 according to the present invention for use in the treatment of sleep apnea in a patient in need thereof.

According to other embodiments, the facial interface 10 of the present invention may be used in most applications that require the administration/delivery of a therapeutic gas, such as for example oxygen. Therefore, additional embodiments include methods for the administration of a therapeutic gas to a patient in need thereof, comprising the step of contacting a patient's face with a facial interface 10 according to the present invention, prior to administration of the therapeutic gas with a gas administration device.

Also encompassed are methods for the administration of a therapeutic gas or substance to a patient in need thereof, comprising the step of administering the therapeutic gas to the patient with a gas administration device and a facial interface 10 according to the present invention.

Also encompassed is the use of the facial interface 10 according to the present invention, and a gas administration device, for administration of a therapeutic gas to a patient in need thereof, and a facial interface according to the present invention for use in the administration of a therapeutic gas or substance to a patient in need thereof.

The present invention will be more readily understood by referring to the following examples which are given to illustrate the invention rather than to limit its scope.

While preferred embodiments have been described above and illustrated in the accompanying drawings, it will be evident to those skilled in the art that modifications may be made without departing from this disclosure. Such modifications are considered as possible variants comprised in the scope of the disclosure.

The invention claimed is:

1. A facial interface comprising:
a flexible face contact layer configured to cover a user's face and comprising a contact free overlay of an ocular region of a user's face which comprises a slot and a flap, said flap configured to fold away from said ocular region, to allow said user to see through said facial interface; and
a nasal layer configured to sealably cover an external nose region of said user,
wherein said flexible face contact layer and said nasal layer do not impede circulation of air through said user's nostrils.

2. The facial interface of claim 1, wherein said flexible face contact layer is further configured to cover a neck region, a forehead, a temporal region, a cheek region, a jaw region, a chin region, of a user's face, or combinations thereof.

3. The facial interface of claim 1, wherein said flexible face contact layer is further configured to cover said external nose region.

4. The facial interface of claim 1, wherein said flexible face contact layer is further configured to cover said external nose region of said user and provide fluid circulation of air through said user's nostrils.

5. The facial interface of claim 1, wherein said flexible face contact layer and/or said nasal layer is opened over said nostrils of said user, or wherein said flexible face contact layer and/or said nasal layer further comprises a breathable overlay over said nostrils of said user.

6. The facial interface of claim 1, wherein said flexible face contact layer and/or said nasal layer is configured to cover a base of the eye area, cover a bridge of the nose, around the nose and nostrils, or a combination thereof.

7. The facial interface of claim 1, wherein said flexible face contact layer and/or said nasal layer further comprises a sub-nasal tab for coverage of a contour of said nose and nostrils.

8. The facial interface of claim 7, wherein said sub-nasal tab comprises a pair of sub-nasal tabs, with one sub-nasal tab on each side of each nostrils, without joining under said nose or wherein said sub-nasal tab comprises a single sub-nasal tab joining under said nose.

9. The facial interface of claim 1, wherein said nasal layer is laminated over said flexible face contact layer.

10. The facial interface of claim 1, further comprising a flexible external layer, contacting said flexible face contact layer and/or said nasal layer, configured to modulate thickness of said facial interface.

11. The facial interface of claim 1, further comprising a nasal padding layer, to provide padding to said nasal layer.

12. The facial interface of claim 1, further comprising a cervical wing, configured to cover a neck region.

13. The facial interface of claim 12, wherein said cervical wing is a pair of cervical wings configured to cover both sides of a neck region.

14. The facial interface of claim 1, further comprising an auricular clearance, configured to provide clearance between ears of the user and said facial interface.

15. The facial interface of claim 1, further comprising a grip layer to provide adherence and prevent slippage of an overlaid mask from said facial interface, and wherein said grip layer is configured to cover said external nose region, a neck region, a temporal region, a forehead region, and combinations thereof.

16. The facial interface of claim 1, further comprising means to maintain said facial interface in place on a user's head.

17. The facial interface of claim 1, wherein said facial interface is configured as having a thickness tapering off toward an outline thereof, to avoid marking of said user's skin from use of said facial interface.

* * * * *